US00PP37521P2

(12) United States Plant Patent
Biancheri

(10) Patent No.: US PP37,521 P2
(45) Date of Patent: Jul. 14, 2026

(54) ***RANUNCULUS* PLANT NAMED 'AB LATONIN'**

(50) Latin Name: *Ranunculus asiaticus*
Varietal Denomination: AB LATONIN

(71) Applicant: Biancheri Creazioni Societa' Semplice Agricola, Camporosso Mare (IT)

(72) Inventor: Alberto Biancheri, Camporosso Mare (IT)

(73) Assignee: Biancheri Creazioni Societa' Semplice Agricola (IT)

( * ) Notice: Subject to any disclaimer, the term of this patent is extended or adjusted under 35 U.S.C. 154(b) by 0 days.

(21) Appl. No.: 19/357,311

(22) Filed: Oct. 14, 2025

(51) Int. Cl.
*A01H 6/72* (2018.01)
*A01H 5/02* (2018.01)

(52) U.S. Cl.
USPC ..... Plt./263.1

(58) Field of Classification Search
USPC ..... Plt./263.1
CPC ..... A01H 6/72; A01H 5/02
See application file for complete search history.

*Primary Examiner* — Keith O. Robinson

(57) ABSTRACT

A new and distinct cultivar of *Ranunculus* plant named 'AB LATONIN' is disclosed characterized by White NN155A flowers with a densely spiraled shape. Flower petals are durable and spread out broad and flat, rather than cup-shaped. The durability of the flower petal includes resistance to damage caused by *Botrytis*. The new variety is a *Ranunculus*. normally produced as a cut flower and potentially useful as an ornamental plant.

2 Drawing Sheets

Figure 1:
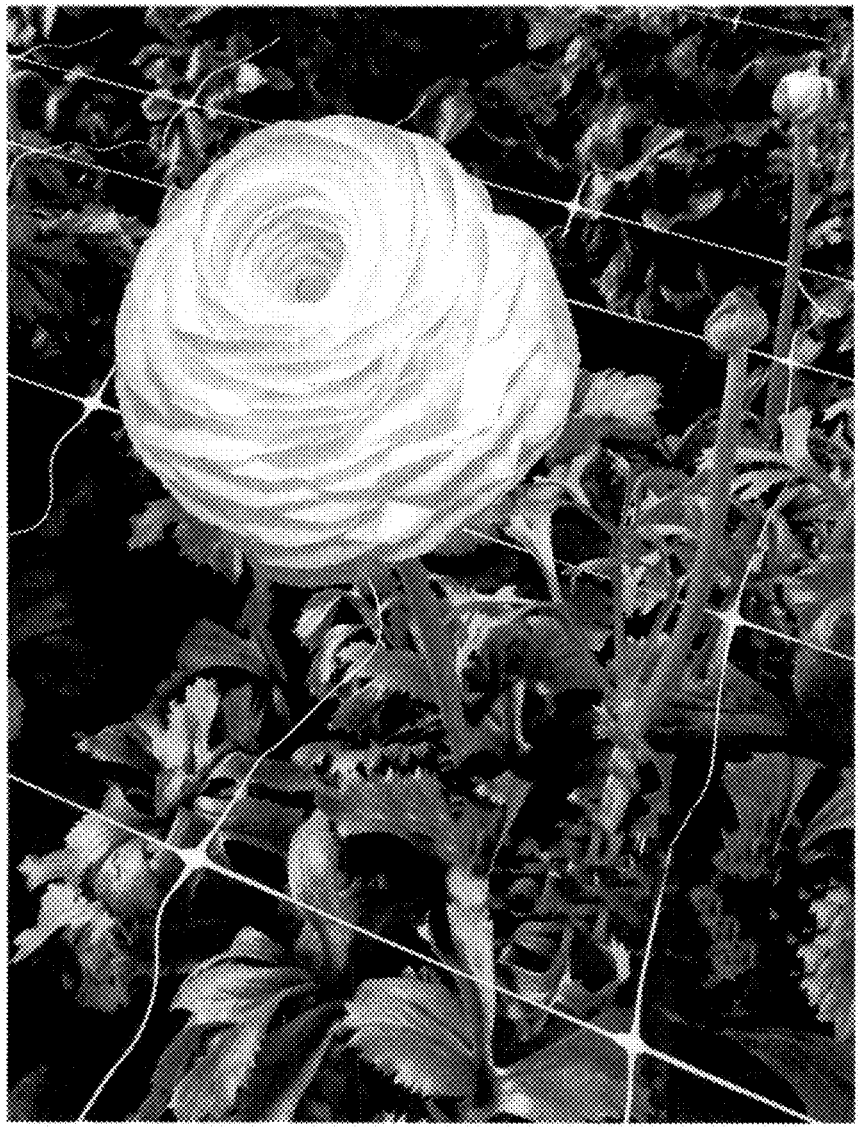

Latin name of the genus and species: *Ranunculus asiaticus*.

Variety denomination: 'AB LATONIN'.

BACKGROUND OF THE INVENTION

The new *Ranunculus* cultivar is a product of a planned breeding program conducted by the inventor, Alberto Biancheri at a research nursery in Camporosso Mare, Italy. The cross resulting in this new variety was made during 2013.

The seed parent is an unnamed, unpatented, proprietary *Ranunculus asiaticus*. The pollen parent is a different unnamed, unpatented, proprietary *Ranunculus asiaticus*. The new variety was selected in 2016 by the inventor in a group of seedlings resulting from the 2013 crossing, in a research greenhouse in Camporosso Mare, Italy.

Asexual reproduction of the new cultivar was first performed by vegetative division of buds sprouting from the rhizome of the selected plant. Subsequent propagation has been performed by tissue culture. First propagation took place at a research greenhouse in Camporosso Mare, Italy in 2016 and has shown that the unique features of this cultivar are stable and reproduced true to type in multiple successive generations.

SUMMARY OF THE INVENTION

The cultivar 'AB LATONIN' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'AB LATONIN'. These characteristics in combination distinguish 'AB LATONIN' as a new and distinct *Ramunculus* cultivar:

1. White NN155A flower color.
2. Densely whorled flower shape.
3. Vegetative, herbaceous plant habit.
4. Long flower stems.
5. High number of flower stems per plant.
6. Durable flower petals.

PARENT COMPARISON

Plants of the new cultivar 'AB LATONIN' are similar to plants of the seed parent, in most horticultural characteristics, however, plants of the new cultivar 'AB LATONIN' differ in the following;

1. Plants of the new cultivar are not as compact as plants of the seed parent.
2. Flower stems of the new cultivar are 10 to 15 cm longer than flower stems of the seed parent.
3. Plants of the new cultivar produce 5 to 10 more flowering stems than plants of the seed parent during the production season.

Plants of the new cultivar 'AB LATONIN' are similar to plants of the pollen parent, in most horticultural characteristics, however, plants of the new cultivar 'AB LATONIN' differ in the following;

1. Flowers of the new variety are a different shape than those of the pollen parent. Flowers of the new cultivar are densely whorled, with petals that open flat, rather than cupped.
2. Flower stems of the new cultivar are 5 to 10 longer than flower stems of the pollen parent.
3. Petals of the new cultivar are more durable and resistant to spotting than petals of the pollen parent.

COMMERCIAL COMPARISON

Plants of the new cultivar 'AB LATONIN' are comparable to the unpatented commercial variety *Ranunculus* 'ABME- NEO'. The two *Ranunculus* varieties are similar in most horticultural characteristics; however, the new variety 'AB LATONIN' differs in the following:

1. Plants of the new cultivar have a vegetative habit not found in this comparator.
2. Flower color or the new cultivar is NN155A; flower color of this comparator is NN155D.
3. Flower shape of the new cultivar is less cupped than flower shape of this comparator.
4. Plants of the new cultivar produce more flowering stems than plants of this comparator.

BRIEF DESCRIPTION OF THE PHOTOGRAPHS

The accompanying photograph in FIG. 1 illustrates in full color flowering plants of the new variety at approximately six months old, grown in a greenhouse during March in Camporosso, Italy.

Figure 2:
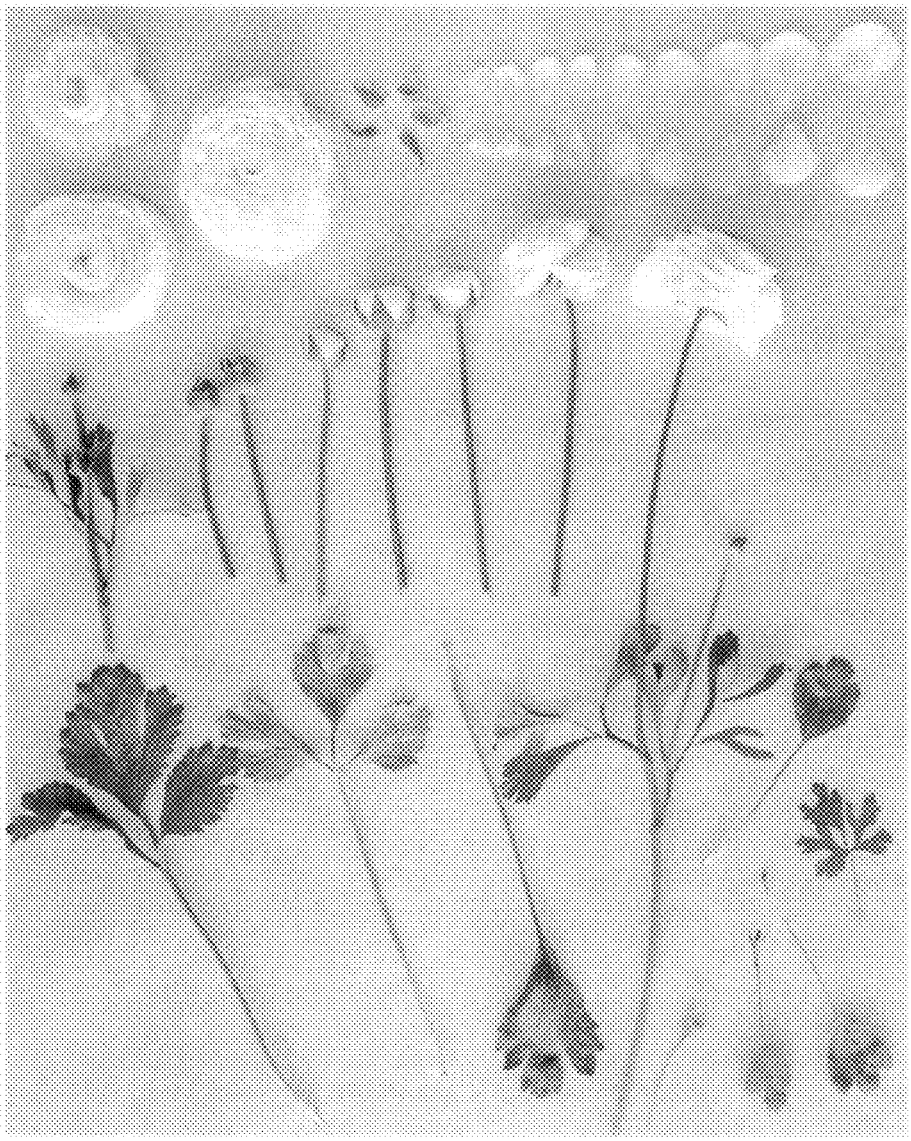

FIG. 2 illustrates various floral and foliar parts.

The photographs were taken using conventional techniques and although colors may appear different from actual colors due light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe plants of 'AB LATONIN' planted in the month of September in a greenhouse in Camporosso Mare, Italy. The plant has been described in the month of March. In order to protect the crop against pests, some chemical treatments are performed. Treatments with growth regulators can be performed to limit the plant sizes. In particular, no growth regulators have been applied on the plant described. The rhizome has been planted on raised benches in a peat and pumice substrate mixture. The growing temperature ranged from 12° C. to 25° C. during the day and from 2° C. to 8° C. during the night. General light conditions are bright, normal sunlight. Measurements and numerical values represent averages of typical plant types.

Botanical classification: *Ranunculus asiaticus* 'AB LATONIN'.

PROPAGATION

Time to rooting: 15 days at approximately 10-12° C.

Time to produce a rooted plantlet: 20 days.

Root description: Secondary roots grow by rhizome and are fasciculate type.

PLANT

Age of the plant described: About 5 months.

Growth habit: Herbaceous perennial, robust plant, semi-prostrate vegetation.

Height to top flower: 85 to 100 cm.

Plant spread: 50 to 60 cm.

Branching characteristics: Main floral stems grow from a basal rosette with 1 or 2 lateral branches, each one of which has 1 to 3 flowers.

Length of lateral branches: 45 to 55 cm.

Diameter of lateral branches: 0.4 to 1.0 cm.

Texture of lateral branches: Glossy, slightly tomentose.

Internode length: No internodes, basal rosette.

Strength of lateral branches: Moderate.

Color of lateral branches: Strong Yellow Green (RHS 144A).

Angle of branches: 25° to 30°.

Number of leaves per lateral branch: Usually 2 or 4.

FOLIAGE

The plant has a marked heterophylly in relation to the degree of their development and their position on the plant (base of the plant; floral stem). The same plant may have leaves of different size and arrangement (simple, ternate and biternate), in relation to the degree of development (young leaf and mature leaf) and their position on the plant.

Leaf at the base of the plant:

*Arrangement.*—Simple-Biternate young leaf; Biternate mature leaf.

*Average length.*—30-35 cm.

*Average width.*—18-25 cm.

*Overall shape of blade.*—Obovate (young leaf); Palmatipartite (mature leaf).

*Dissected leaves, describe lobes, quantity of dissection.*—The young leaves are generally not lobed, while the mature leaves are typically divided into 3 sections, each of which is further subdivided into 3 lobes.

*Apex.*—Acute.

*Base.*—Attenuate.

*Attachment.*—Petiolate.

*Margin.*—Dentate.

*Texture of top surface.*—Slightly tomentose.

*Texture of bottom surface.*—Slightly tomentose.

*Appearance of top surface.*—Slightly glossy.

*Appearance bottom surface.*—Slightly glossy.

*Leaf internode length.*—The internodes are extremely close together, forming a basal rosette.

*Color.*—Young foliage upper side: Moderate Olive Green (RHS 137B). Young foliage under side: Moderate Yellow Green (RHS 138A-138B). Mature foliage upper side: Moderate Olive Green (RHS 137B). Mature foliage under side: Moderate Yellow Green (RHS 138A and 138B).

*Venation.*—Type: Dichotomous; plunging into the limb at the upper surface; raised on the limb at the lower surface. Venation color upper side: Strong Yellow Green (RHS 144A). Venation color under side: Strong Yellow Green (RHS 144A).

*Petiole.*—Petiole: Tubular, slightly flattened. Length: 20-25 cm. Diameter: 0.5-0.8 cm. Pubescence: Slightly tomentose. Color: Strong Yellow Green (RHS 144A).

Leaf inserted at the nodes of the floral stems:

*Arrangement.*—Biternate.

*Average length.*—10-15 cm.

*Average width.*—10-15 cm.

*Overall shape of blade.*—Palmatipartite.

*Dissected leaves, describe lobes, quantity of dissection.*—Generally divided in 3 parts, each one of which further divided in many deeply incised lobes.

*Apex.*—Acute.

*Base.*—Acute.

*Attachment.*—Petiolate.

*Margin.*—Dentate.

*Texture of top surface*.—Slightly tomentose.
*Texture of bottom surface*.—Slightly tomentose.
*Appearance of top surface*.—Matte.
*Appearance bottom surface*.—Glossy.
*Leaf internode length*.—8-12 cm.
*Color*.—Foliage upper side: Moderate Olive Green (RHS 137B). foliage under side: Moderate Yellow Green (RHS 137C).
*Venation*.—Type: Dichotomous, plunging into the limb at the upper surface and raised on the limb at the lower surface. Venation color upper side: Strong Yellow Green (RHS 144A). Venation color under side: Strong Yellow Green (RHS 144A).
*Petiole*.—Petiole: Slightly flat. Length: 3-5 cm. Diameter: 0.4-0.6 cm. Pubescence: Slightly tomentose. Color: Strong Yellow Green (RHS 144A).

FLOWER

Bloom period: Winter-Spring.
Vase life (cut flower): 10-15 days.
Persistent or self-cleaning: Self-Cleaning.
Bud:
*Closed bud*.—Shape: Flattened globular. Length: 0.5-0.7 cm. Diameter: 0.5-0.8 cm. Color: Moderate Yellow Green (RHS 137C).
*Slightly open bud*.—Shape: Flattened globular. Length: 0.6-1.2 cm. Diameter: 1.1-1.3 cm. Color: Yellowish White (RHS NN155A).
Flower size:
*Diameter*.—5-9 cm.
*Height*.—2.5-3.5 cm.
Corolla: Round, symmetrical, flattened.
*Petals*.—
*Arrangement*.—Imbricated, disposed on the receptacle in very tight verticils. The size of the petals is quite variable. according to the position in the corolla. decreasing from the exterior toward the center. The average size of fully developed petal is as follows.
*Petal length*.—2.5-5.5 cm.
*Petal width*.—2.0-4.5 cm.
*Quantity*.—Double flower. petals are very numerous (>100).
*Texture*.—Silky, thin. Resistant to tearing.
*Petal apex*.—Rounded.
*Pet shape*.—Obovate.
*Margin*.—Entire-Finely Crenate.
*Aspect*.—Concave with moderately reflexed apex when flower is fully opened.
*Color when opening*.—
*Upper surface*.—Light Yellow Green (RHS 145D).
*Lower surface*.—Light Yellow Green (RHS 145D).
*Color fully opened*.—
*Upper surface*.—Yellowish White (RHS NN155A); Light Yellow Green (RHS 145D) at the base.
*Lower surface*.—Yellowish White (RHS NN155B); Light Yellow Green (RHS 145D) at the base.
Calyx-Sepals:
*Quantity per flower*.—5.
*Shape*.—Concave incurved at the apex.
*Length*.—1.5-2.2 cm.
*Width*.—0.7-1.0 cm.
*Apex*.—Slightly acute to rounded.
*Base*.—Truncate.
*Margin*.—Entire.
*Texture*.—Lower surface is tomentose; Upper surface is glabrous.
*Color upper surface*.—Strong Yellow Green (RHS 144A).
*Color lower surface*.—Moderate Yellow Green (RHS 146D); Strong Yellow Green (RHS 144A near the base.
Peduncle: None.
Pedicel:
*Length*.—40-45 cm.
*Diameter*.—0.5-1.0 cm.
*Color*.—Strong Yellow Green (RHS 144A).
*Orientation*.—Upright. Straight, rigid.
*Pubescence*.—Slightly tomentose.
Fragrance.—None.

REPRODUCTIVE ORGANS

Androecium: Stamens are almost completely transformed to petals. Very infrequently small, malformed stamens can be found in some flowers at the end of the flowering.
Gynoecium: The pistils are numerous, short, locked together at the center of the corolla in a Light Yellow Green (RHS 145B) mixed with Strong Yellow Green (RHS 145A) cone-shaped apocarpous gynoecium.
Nectar glands: Absent.

OTHER CHARACTERISTICS

Disease and pests: The durability of the flower petals make them resistance to spotting, including damage from *Botrytis*. No other resistance or susceptibility observed.
Drought tolerance and cold tolerance: No differences have been noted in comparison to the common tolerance characteristics to other *Ranunculus* cultivars.
Fruit-Seed production: Not observed.

What is claimed is:

1. A new and distinct cultivar of *Ranunculus* plant named 'AB LATONIN' as herein illustrated and described.

* * * * *